(12) United States Patent  
Konstorum et al.

(10) Patent No.: US 8,967,204 B2  
(45) Date of Patent: Mar. 3, 2015

(54) CURVED PIPE FOR ENDOSCOPES

(71) Applicant: Olympus Medical Systems Corp., Tokyo (JP)

(72) Inventors: Gregory S. Konstorum, Stamford, CT (US); Eijiro Sato, Tokyo (JP)

(73) Assignee: Olympus Medical Systems Corporation, Tokyo (JP)

( * ) Notice: Subject to any disclaimer, the term of this patent is extended or adjusted under 35 U.S.C. 154(b) by 111 days.

(21) Appl. No.: 13/770,381

(22) Filed: Feb. 19, 2013

(65) Prior Publication Data

US 2014/0053940 A1 Feb. 27, 2014

Related U.S. Application Data

(60) Provisional application No. 61/692,930, filed on Aug. 24, 2012.

(51) Int. Cl.
- *F16L 11/00* (2006.01)
- *A61M 25/01* (2006.01)
- *A61B 1/005* (2006.01)

(52) U.S. Cl.
CPC ............ *F16L 11/00* (2013.01); *A61M 25/0138* (2013.01); *A61B 1/0055* (2013.01); *A61B 1/0057* (2013.01)
USPC .......................................... 138/119; 600/139

(58) Field of Classification Search
CPC .. A61B 1/0051; A61B 1/0055; A61B 1/0056; A61B 1/0057; A61M 25/0133; A61M 25/0138; F16L 11/00
USPC ........... 138/118, 119; 600/101, 139, 141, 585
See application file for complete search history.

(56) References Cited

U.S. PATENT DOCUMENTS

| 5,381,782 A * | 1/1995 | DeLaRama et al. .......... 600/149 |
| 6,749,560 B1 | 6/2004 | Konstorum et al. |
| 8,663,090 B2 * | 3/2014 | Fujimoto ...................... 600/114 |
| 2003/0023142 A1 | 1/2003 | Grabover et al. |
| 2005/0273085 A1 | 12/2005 | Hinman et al. |

FOREIGN PATENT DOCUMENTS

| EP | 2 596 742 A1 | 5/2013 |
| JP | 09-288239 | 11/1997 |
| JP | 10-94514 A | 4/1998 |
| JP | 2001-161631 A | 6/2001 |
| JP | 2003-250762 A | 9/2003 |
| JP | 2008-295773 A | 12/2008 |
| JP | 2012-125588 A | 7/2012 |
| WO | 2005/120327 A2 | 12/2002 |
| WO | 2005/120326 A2 | 12/2005 |
| WO | 2008/146510 A1 | 12/2008 |

* cited by examiner

*Primary Examiner* — J. Casimer Jacyna  
(74) *Attorney, Agent, or Firm* — Scully, Scott, Murphy & Presser, PC

(57) ABSTRACT

In a bending tube including: multiple first slots for bending provided at set intervals, respectively, along a direction of a direction of a longitudinal axis O of a cylindrical bending tube body, the multiple first slots for bending extending in a circumferential direction of the bending tube body; slots for forming wire guide (a first slot for bending) paired and provided on arrangement of the multiple first slots for bending, the slots for forming wire guide extending in the circumferential direction of the bending tube body; and a wire guide formed by deforming a circumferential part of the bending tube body between the paired slots for forming wire guide, in an inner diameter direction; a width of a slot for bending adjacent to the wire guide is set relatively narrower than a width of other slots for bending.

10 Claims, 25 Drawing Sheets

CURVED PIPE FOR ENDOSCOPES

CROSS REFERENCE TO RELATED APPLICATION

This application claims benefit of Provisional Application No. 61/692,930 filed on Aug. 24, 2012, the contents of which are incorporated by this reference.

BACKGROUND OF THE INVENTION

1. Field of the Invention

The present invention relates to a bending tube for endoscope (i.e. curved pipe for endoscopes) that performs a bending movement according to an operation of an operation section.

2. Description of the Related Art

An endoscope with which an image of an object in a body cavity is displayed on a screen of a display device by inserting an elongated insertion section into the body cavity has been conventionally used widely. For example, in a flexible endoscope the insertion section of which has flexibility, among endoscopes of that kind, the insertion section is configured such that a distal end rigid portion, a bending section and a flexible tube section are provided in a coupled manner in that order from the distal end side.

The bending section is configured to be bendable, for example, in two directions of up and down directions, two directions of right and left directions, or four directions of up, down, right and left directions associated with the object image displayed on the display device. In order to enable such a bending movement, the bending section is generally configured being provided with a bending tube (a set of bending sections) with multiple joint pieces rotatably coupled via rotation pins. An angle wire is inserted in the bending tube, and a bending movement of the bending section is performed by pulling or releasing the angle wire.

Recently, a bending tube using superelastic alloy material is proposed as a bending tube simply configured without using joint pieces and rotation pins. This kind of bending tube is configured by providing multiple slots on a cylindrical pipe material (a bending tube body) using laser processing or the like, for example, as disclosed in Japanese Patent Application Laid-Open Publication No. 9-288239. Furthermore, in order to simplify the configuration of the bending tube more, a technique of integrally forming a wire supporter (a wire guide) for inserting an angle wire by deforming a part of a ring-shaped part of the pipe material in an inner diameter direction of the pipe material is disclosed in Japanese Patent Application Laid-Open Publication No. 9-288239.

SUMMARY OF THE INVENTION

According to one aspect of the present invention, there is provided a bending tube for endoscope including: a cylindrical bending tube body made of superelastic alloy material; multiple slots for bending provided at set intervals, respectively, along a direction of a longitudinal axis of the bending tube body, the multiple slots for bending extending in a circumferential direction of the bending tube body; slots for forming wire guide paired and provided on arrangement of the multiple slots for bending, the slots for forming wire guide extending in the circumferential direction of the bending tube body; and a wire guide formed by deforming a circumferential part of the bending tube body between the paired slots for forming wire guide, in an inner diameter direction; wherein a width of a slot for bending, among the multiple slots for bending, adjacent to the wire guide is set narrower than a width of other slots for bending.

DETAILED DESCRIPTION OF THE PREFERRED EMBODIMENTS

Figure 1:
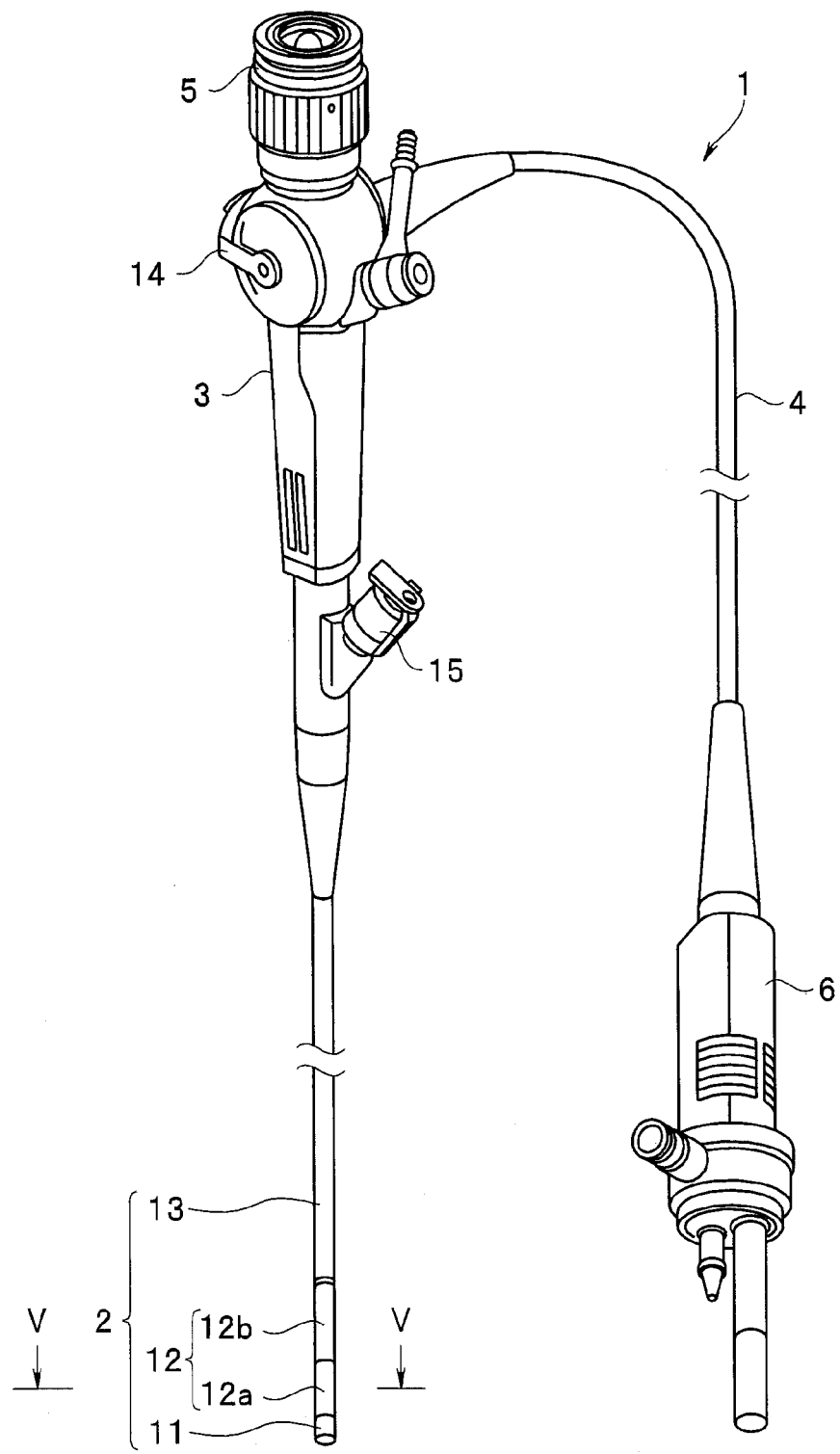
FIG. 1 relates to a first embodiment of the present invention and is a perspective view of an endoscope.
Figure 2:
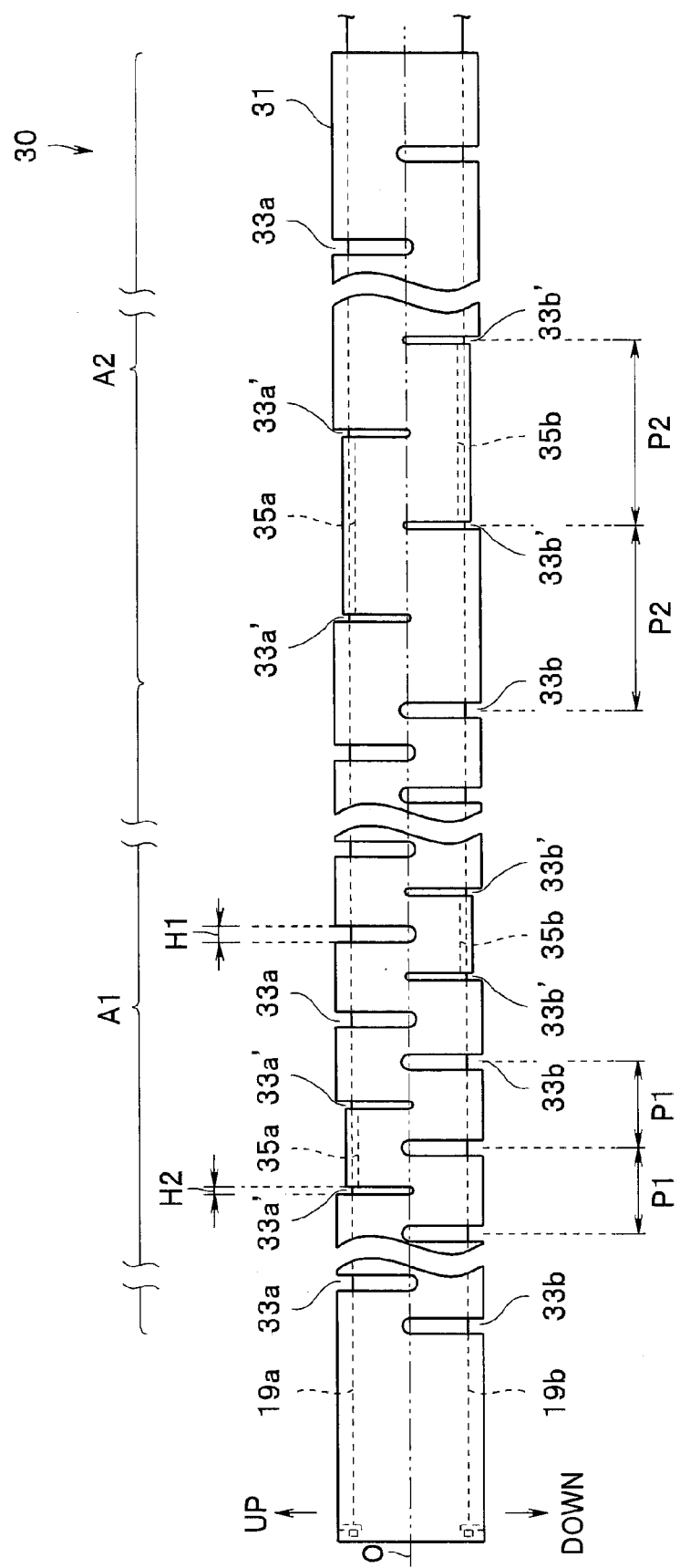
FIG. 2 relates to the first embodiment of the present invention and is a side view of a bending tube.
Figure 3:
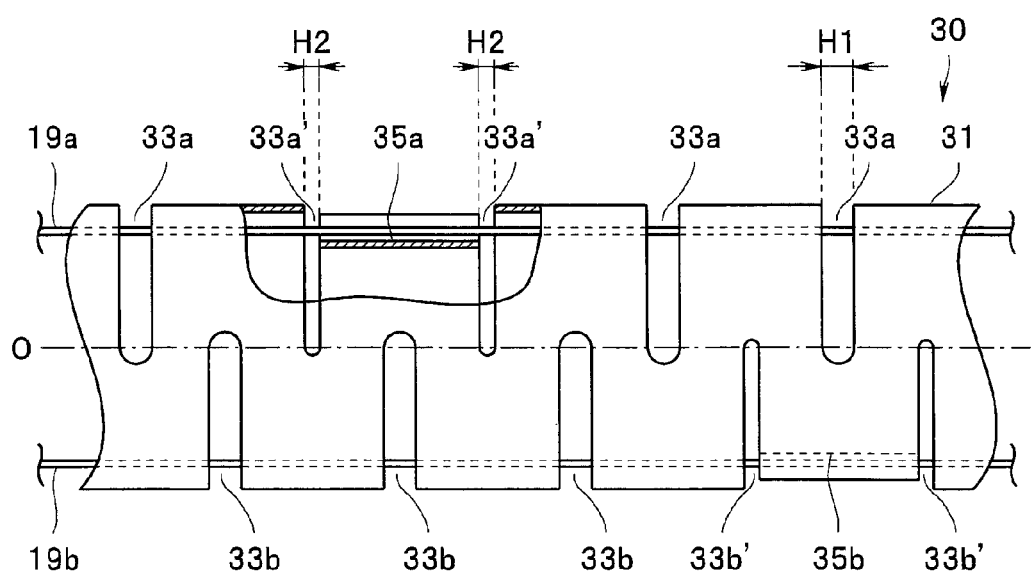
FIG. 3 relates to the first embodiment of the present invention and is a side view showing a cutaway of a portion of a main part of the bending tube.
Figure 4:
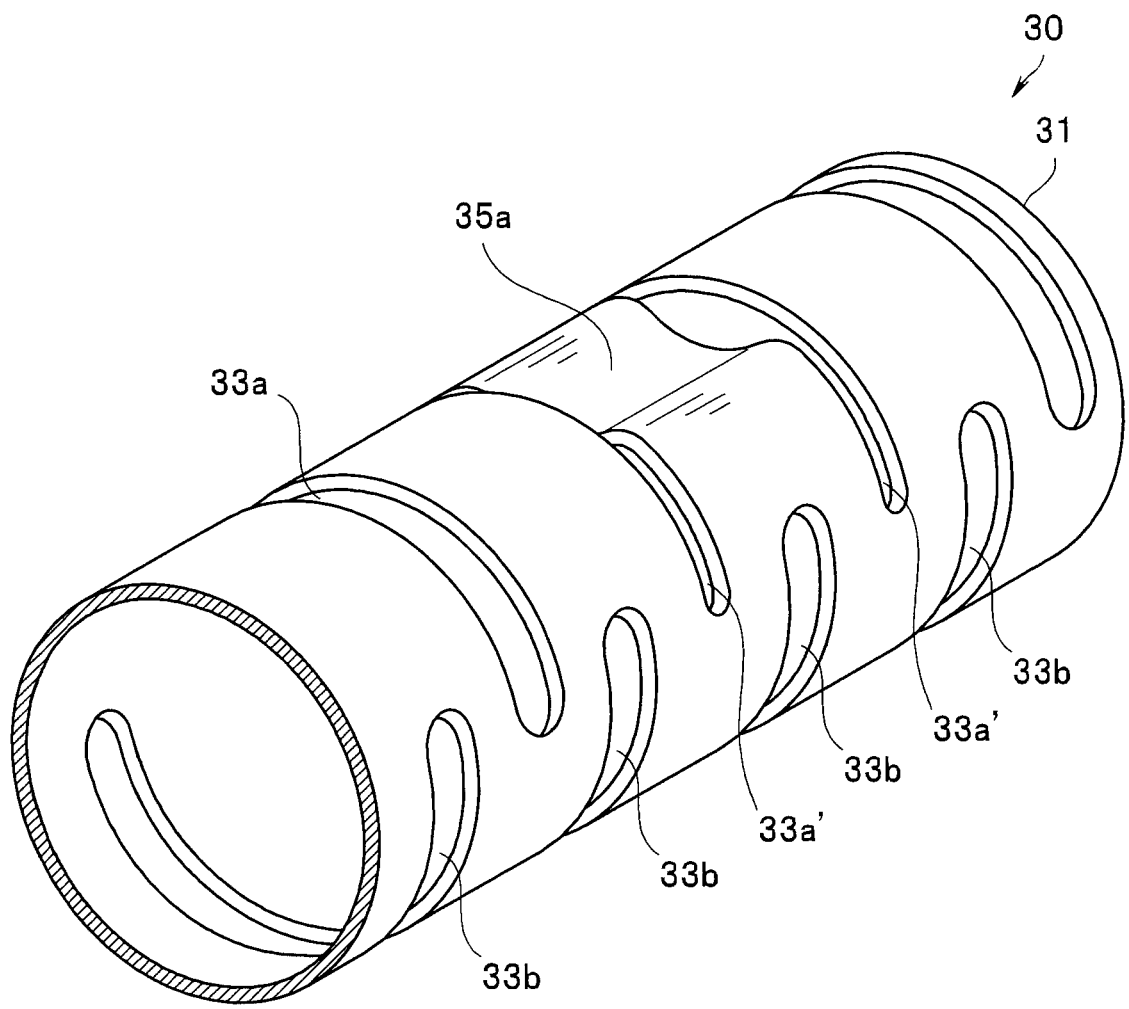
FIG. 4 relates to the first embodiment of the present invention and is a perspective view showing the main part of the bending tube.
Figure 5:
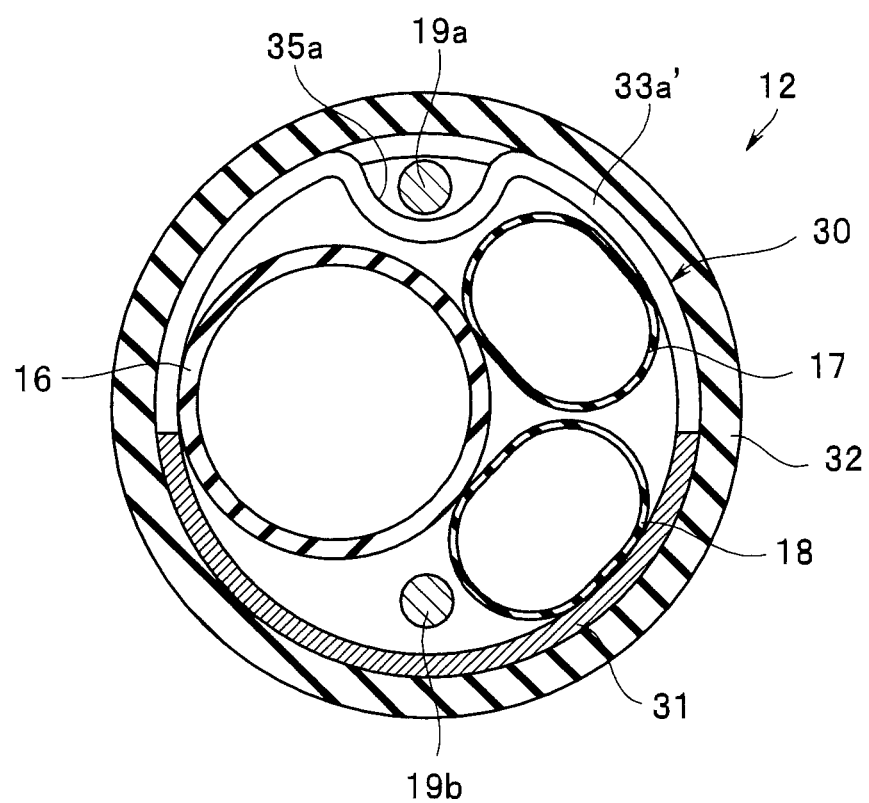
FIG. 5 relates to the first embodiment of the present invention and is a cross-sectional view of the main part along a V-V line in FIG. 1.
Figure 6:
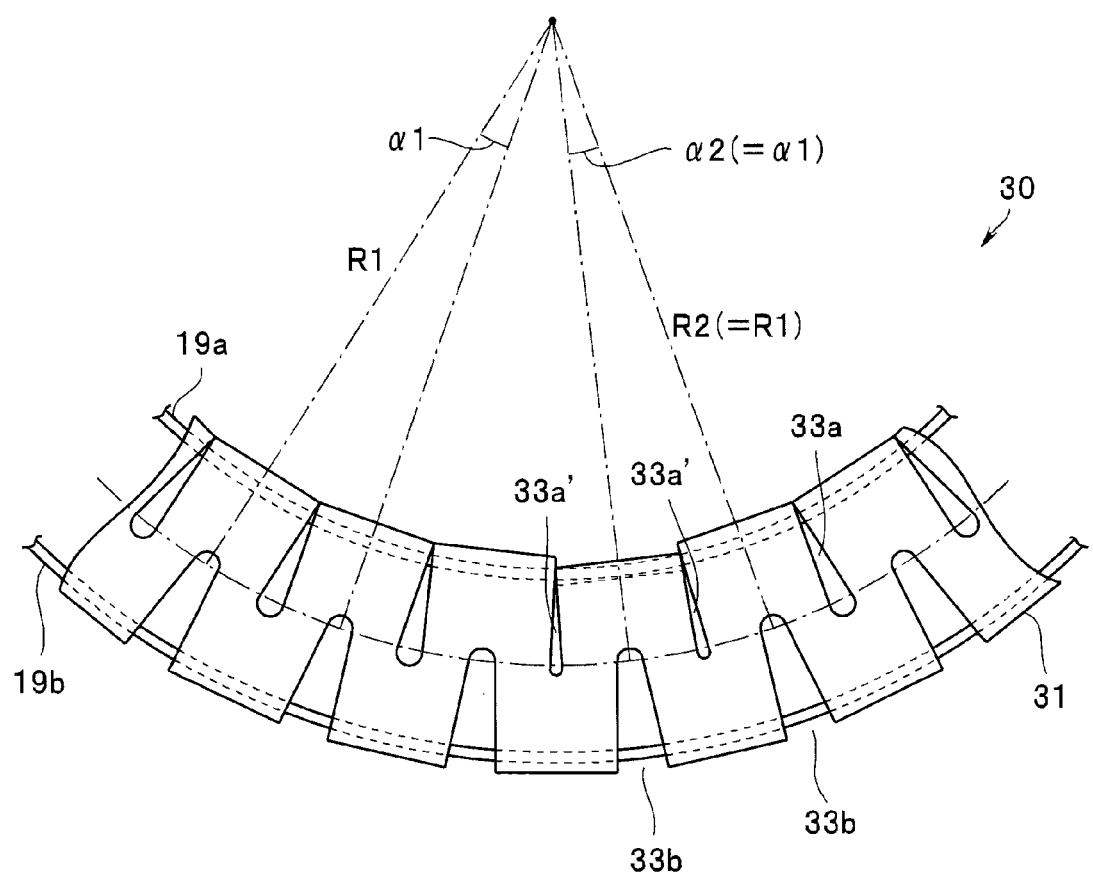
FIG. 6 relates to the first embodiment of the present invention and is a diagram showing a minimum radius of curvature of the bending tube.
Figure 7:
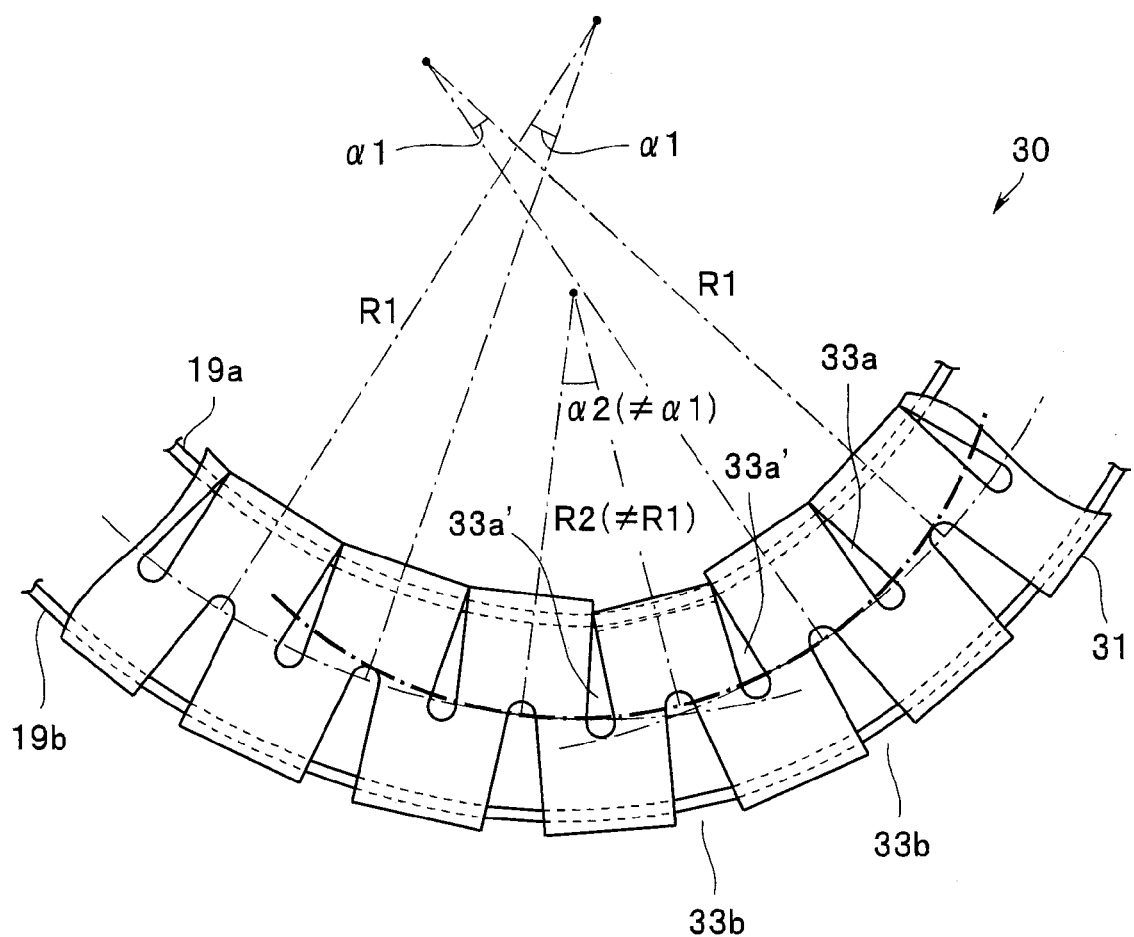
FIG. 7 relates to the first embodiment of the present invention and is a diagram showing the minimum radius of curvature of the bending tube in the case of a slot width not being adjusted, as a comparative example.

Embodiments of the present invention will be described below with reference to drawings. Drawings relate to a first embodiment of the present invention. FIG. 1 is a perspective view of an endoscope; FIG. 2 is a side view of a bending tube; FIG. 3 is a side view showing a cutaway of a portion of a main part of the bending tube; FIG. 4 is a perspective view showing the main part of the bending tube; FIG. 5 is a cross-sectional view of the main part along a V-V line in FIG. 1; FIG. 6 is a diagram showing a minimum radius of curvature of the bending tube; and FIG. 7 is a diagram showing the minimum radius of curvature of the bending tube in the case of a slot width not being adjusted, as a comparative example.

As shown in FIG. 1, an endoscope 1 is a so-called fiber scope, a main part of which is configured being provided with, for example, a long insertion section 2 to be inserted into a subject, an operation section 3 provided at a proximal end of the insertion section 2, a universal cord 4 extending from a lateral part of the operation section 3, an eye piece section 5 provided at a proximal end of the operation section 3, and a connector 6 provided at an extension end of the universal cord 4. Note that the endoscope 1 can be connected to an external apparatus (not shown) such as a light source apparatus via the connector 6. Though a configuration of the endoscope 1 will be described with a configuration of a fiber scope as an example, in the present embodiment, the endoscope 1 to which the present invention is applied is, of course, not limited to a fiber scope.

A main part of the insertion section 2 is configured being provided with a distal end rigid portion 11 positioned on a distal end side, a bending section 12 provided being coupled with a proximal end of the distal end rigid portion 11, and a flexible tube section 13 having flexibility and coupled with a proximal end of the bending section 12.

Note that a lens for observation, a lens for illumination and the like not shown are provided inside the distal end rigid portion 11.

The bending section 12 can be freely bent, for example, in two directions of up and down directions by a rotation operation of a bending lever 14 provided for the operation section 3 being performed.

The operation section 3 is provided with a treatment instrument insertion opening 15. The treatment instrument insertion opening 15 is connected to a proximal end side of a treatment instrument insertion channel 16 (see FIG. 5) inserted in the insertion section 2. Thereby, a treatment instrument inserted into the treatment instrument insertion opening 15 can be led to the distal end side of the insertion section 2 via the treatment instrument insertion channel 16 and can protrude into a subject from an opening formed on a distal end face of the distal end rigid portion 11.

Here, in addition to the treatment instrument insertion channel 16, a light guide 17 that transmits illumination light to the lens for illumination described above, an image guide 18 that transmits an optical image of the inside of a subject condensed on the lens for observation described above, to the eye piece section 5, angle wires 19a and 19b for causing the bending section 12 to perform a bending movement in conjunction with a rotation operation of the bending lever 14, and the like (see FIG. 5) are inserted in the insertion section 2 and the operation section 3. Note that the light guide 17 is also inserted in the universal cord 4 and the connector 6.

Next, a configuration of the bending section 12 will be described in detail. Note that, in the present embodiment, the bending section 12 is configured by being provided with a first bending section 12a positioned on the distal end side and a second bending section 12b coupled with a proximal end of the first bending section 12a. The first and second bending sections 12a and 12b are different, for example, in the minimum radius of curvature at a time of bending, and the minimum radius of curvature of the first bending section 12a is set shorter than the minimum radius of curvature of the second bending section 12b. The bending section 12 is not limited to such a configuration that the minimum radius of curvature at the time of bending is different between the distal end side and the proximal end side at two stages as described above. For example, a configuration in which the minimum radius of curvature is uniform from the distal end side to the proximal end side is, of course, possible.

As shown in FIGS. 2 to 5, the bending section 12 is configured, for example, being provided with a bending tube 30 a main body of which is a cylindrical bending tube body 31 made of superelastic alloy material, and outer skin 32 which is made of resin and which covers a circumference surface of the bending tube 30. Here, as examples of the superelastic alloy material forming the bending tube body 31, Ni—Ti (nickel titanium), titanium alloy, β-titanium, pure titanium, 64 titanium, A7075 and the like are given; however, the superelastic alloy material is not limited thereto.

On the bending tube body 31, multiple slots for bending, each of which is configured by a long hole in a partial arc shape and extends in a circumferential direction of the bending tube body 31, are provided, for example, by laser processing.

For example, to make a specific description in the present embodiment in which the bending section 12 is bendable in two up/down directions, the bending tube body 31 is provided with multiple slots for bending 33a extending from an upper side to a lower side of a bending direction of the bending tube body 31 and multiple slots for bending 33b extending from the lower side to the upper side of the bending direction of the bending tube body 31. Here, the respective slots for bending 33a and 33b are configured by such long holes in a partial arc shape that the long holes as the slots for bending 33a and the long holes as the slots for bending 33b are in forms in axial symmetry with each other relative to a longitudinal axis O.

As shown in FIG. 2, the respective slots for bending 33a are arranged in a line at pitches P1 set in advance, in a first area A1 set on the bending tube body 31 to correspond to the first bending section 12a, and, furthermore, arranged in a line at pitches P2 (P1<P2) set in advance, in a second area A2 set on the bending tube body 31 to correspond to the second bending section 12b.

Similarly, the respective slots for bending 33b are arranged in a line at the pitches P1 in the first area A1 set on the bending tube body 31, and, furthermore, arranged in a line at the pitches P2 in the second area A2 set on the bending tube body 31.

Here, in the first area A1, the slots for bending 33b are arranged in a state of being offset by half a pitch (P1/2) relative to the slots for bending 33a in a direction of the longitudinal axis O of the bending tube body 31. Similarly, in the second area A2, the slots for bending 33b are arranged in a state of being offset by half a pitch (P2/2) relative to the slots for bending 33a in the direction of the longitudinal axis O of the bending tube body 31. By being offset in the direction of the longitudinal axis O, each slot for bending 33a and each slot for bending 33b are arranged on the bending tube body 31 without interfering with each other.

On the bending tube body 31 of the present embodiment, particular slots for bending 33a paired with and adjoining each other are also used as slots for forming wire guide (Note that, in the description below, the particular slots for bending 33a will be described with the reference numeral thereof attached with "'" in order to distinguish them from other slots for bending 33a.). A part of an upside circumferential part of the bending tube body 31 is deformed in an inner diameter direction between the paired particular slots for bending 33a', and a wire guide 35a through which a middle part of the angle wire 19a is inserted is formed on the bending tube 30 by the deformation (for example, see FIGS. 3 and 4).

Similarly, on the bending tube body 31 of the present embodiment, particular slots for bending 33b paired with and adjoining each other are also used as slots for forming wire guide (Note that, in the description below, the particular slots for bending 33b will be described with the reference numeral thereof attached with "'" in order to distinguish them from other slots for bending 33b.). A part of a downside circumferential part of the bending tube body 31 is deformed in the inner diameter direction between the paired particular slots for bending 33b', and a wire guide 35b through which a middle part of the angle wire 19b is inserted is formed on the bending tube 30 by the deformation.

Note that each of the wire guides 35a and 35b is formed, for example, by positioning and setting the bending tube body 31 on a predetermined processing jig, and performing heat treatment, such as dipping in salt at a high temperature for a predetermined time period, in a state that an appropriate part on the bending tube body 31 (between the paired slots for bending 33a' and between the paired slots for bending 33b') is pressed in the inner diameter direction by the processing jig.

In such a configuration, a minimum radius of curvature R at the time of bending of the bending tube 30 toward the upside and the minimum radius of curvature R at the time of bending of the bending tube 30 toward the downside are determined mainly depending on the slots for bending 33a (and 33a') and mainly depending on the slots for bending 33b (and 33b'), respectively.

That is, for example, when the first area A1 of the bending tube 30 is bent toward the upside, bending of the slots for bending 33a (33a') of the bending tube body 31 is restricted to predetermined extent by front and back wall parts forming the slots for bending 33a (33a') coming into contact with each other. In other words, a maximum bending angle α at each pitch P1 at the slots for bending 33a (33a') of the bending tube body 31 is basically determined by a width of the slots for bending 33a (33a').

However, in the present embodiment in which the wire guide 35a is integrally formed on the bending tube body 31, front and back wall parts forming the particular slots for bending 33a' which are also used as slots for forming wire guide are not level with each other. Therefore, if a width of the particular slots for bending 33a' is the same as a width of the other slots for bending 33a, the timing of the front and back wall parts of the particular slots for bending 33a' coming into contact with each other is later than the timing of the front and back wall parts of the other slots for bending 33a coming into contact with each other. In other words, if the widths are the same, a folding angle $\alpha 2$ at the particular slots for bending 33a' is larger than a folding angle $\alpha 1$ at the other slots for bending 33a, and, as a result, a minimum radius of curvature R2 at predetermined sections before and after the particular slots for bending 33a' is relatively smaller than a minimum radius of curvature R1 at predetermined sections before and after the other slots for bending 33a, for example, as shown in FIG. 7.

In comparison, in the present embodiment, a width H2 of the particular slots for bending 33a' is adjusted to be relatively narrower than a width H1 of the other slots for bending 33a in order to cause the folding angle $\alpha 2$ at the particular slots for bending 33a' to correspond to the folding angle $\alpha 1$ at the other slots for bending 33a, for example, as shown in FIG. 2. Thereby, the minimum radius of curvature R2 at the predetermined sections before and after the particular slots for bending 33a' is equal to the minimum radius of curvature R1 at the predetermined sections before and after the other slots for bending 33a, and the first bending section 12a is bent in a uniform arc shape.

Note that, as for the width H2 of the particular slots for bending 33a' in the second area A2 and the width H2 of the particular slots for bending 33b' in the first and second areas A1 and A2 also, similar adjustment is, of course, performed as shown in FIG. 2 though specific description thereof is omitted.

According to such an embodiment, it is possible to cause the bending section 12 (the bending tube 30) to perform a bending movement in a desired bending shape by a simple configuration, by setting the width H2 of slots for bending 33a' and 33b' adjacent to wire guides 35a and 35b relatively narrower than the width H1 of the other slots for bending 33a and 33b in the bending tube 30 which is provided with: the multiple slots for bending 33a (and the slots for bending 33b) provided at set intervals, respectively, along the direction of the longitudinal axis O of the cylindrical bending tube body 31, the multiple slots for bending extending in the circumferential direction of the bending tube body 31; the slots for forming wire guide (slots for bending 33a' (and slots for bending 33b') paired and provided on arrangement of the multiple slots for bending 33a (and the slots for bending 33b), the slots for forming wire guide extending in the circumferential direction of the bending tube body 31; and the wire guides 35a and 35b formed by deforming a circumferential part of the bending tube body 31 between the slots of the respective pairs of slots for forming wire guide, in an inner diameter direction. That is, even in the case of simplifying the structure by integrally forming the wire guides 35a and 35b on the bending tube body 31, it is possible to cause each section of the bending section 12 (the first bending section 12a and the second bending section 12b) to perform a bending movement uniformly by setting the width H2 of the slots for bending adjacent to the wire guides 35a and 35b (the particular slots for bending 33a' and 33b') to be relatively narrower than the width H1 of the other slots for bending 33a and 33b.

In this case, by using the particular slots for bending 33a' and 33b' among the multiple slots for bending 33a and 33b as slots for forming wire guide, it is possible to integrally form the wire guides 35a and 35b without increasing the number of slots and simplify the configuration of the bending tube 30 more.

Figure 8:
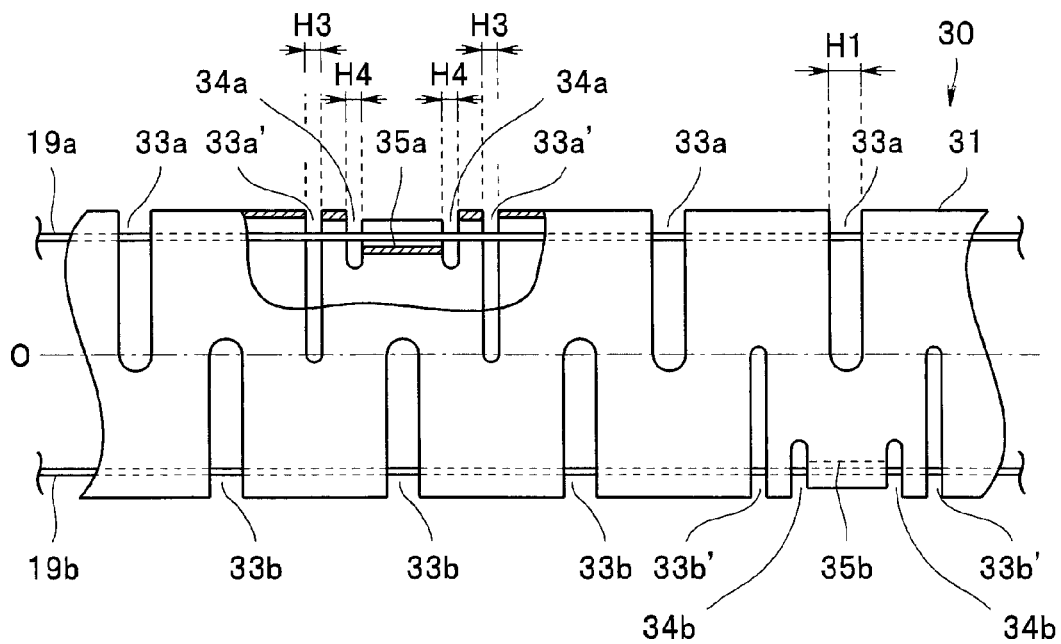
FIG. 8 relates to a second embodiment of the present invention and is a side view showing a cutaway of a portion of a main part of a bending tube.
Figure 9:
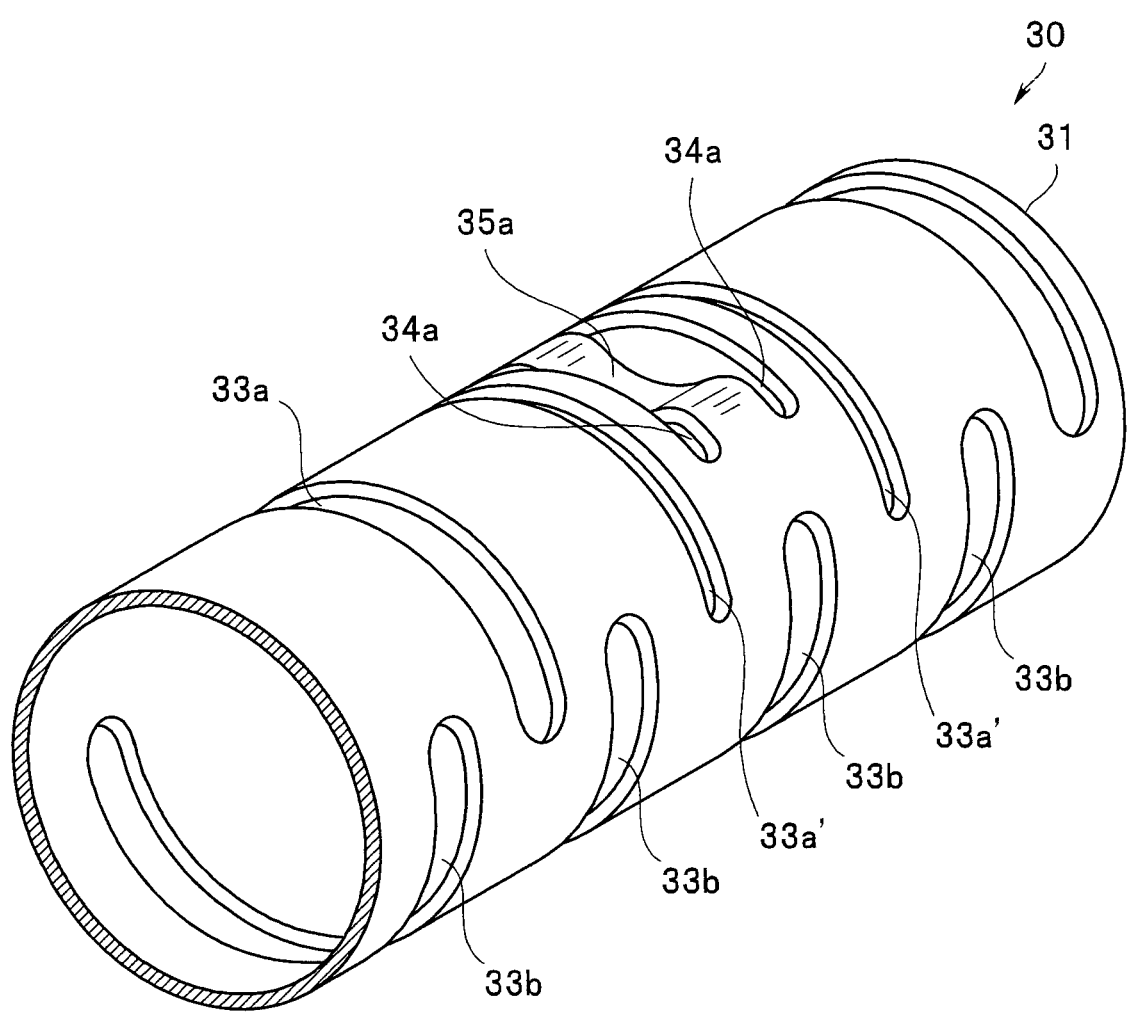
FIG. 9 relates to the second embodiment of the present invention and is a perspective view showing the main part of the bending tube.

Next, FIGS. 8 and 9 relate to a second embodiment of the present invention. FIG. 8 is a side view showing a cutaway of a portion of a main part of a bending tube, and FIG. 9 is a perspective view showing the main part of the bending tube. Note that the present embodiment is different from the first embodiment described above mainly in that slots for forming wire guide are provided separately from slots for bending 33a and 33b. As for other components similar to those of the first embodiment described above, the same reference numerals are given and description will be omitted. The configuration on the upside of a bending tube 30 and the configuration on the downside are almost similar. Therefore, in the present embodiment, mainly the configuration on the upside will be described, and description of the configuration on the downside will be appropriately omitted.

As shown in FIGS. 8 and 9, paired slots for forming wire guide 34a are provided between paired particular slots for bending 33a', among multiple slots for bending 33a, on a bending tube body 31 of the present embodiment.

A part of the circumferential part of the bending tube body 31 is deformed in the inner diameter direction between the paired slots for forming wire guide 34a, and a wire guide 35a through which a middle part of an angle wire 19a is inserted is formed on the bending tube 30 by the deformation.

In the configuration of the present embodiment in which the slots for forming wire guide 34a and 34b are provided separately as described above, rigidity of the bending tube body 31 at a part where the slots for forming wire guide 34a and 34b are provided partially decreases because superelastic alloy material is used. Such partial decrease in the rigidity also affects a bending characteristic of the bending tube 30.

Therefore, in the present embodiment, a width H3 of the particular slots for bending 33a' and 33b' adjacent to the slots for forming wire guide 34a and 34b is set relatively narrower than a width H1 of the other slots for bending 33a and 33b, and the bending characteristic of the bending tube 30 is equalized by adjustment of the width H3.

In this case, it is desirable that a width H4 of the slots for forming wire guide 34a and 34b be set narrower relative to the widths H1 and H3. Furthermore, as for an extended length of the slots for foaming wire guide 34a and 34b, it is desirable that the length thereof be set shorter than those of the slots for bending 33a and 33b as much as possible within such a range that formation of the wire guides 35a and 35b is not interfered therewith.

According to such an embodiment, an effect is obtained that, since difference in level does not occur between front and back wall parts of the particular slots for bending 33a' and 33b', it is possible to uniform the bending characteristic of the bending tube 30 without largely changing the width H3 relative to the width H1, in addition to the effects obtained in the first embodiment described above.

Figure 10:
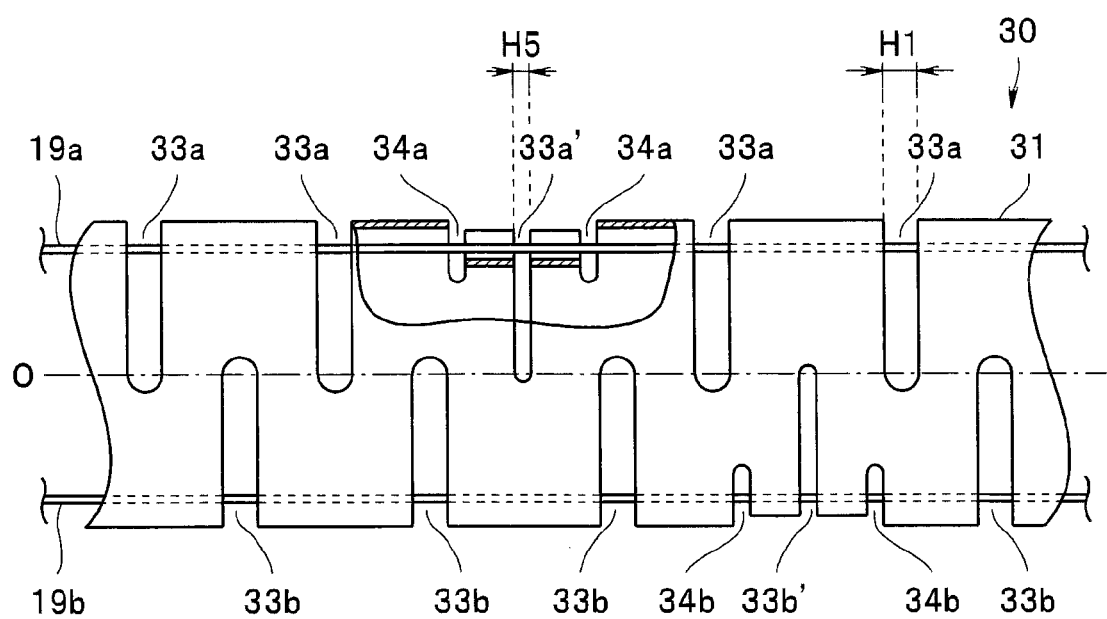
FIG. 10 relates to a third embodiment of the present invention and is a side view showing a cutaway of a portion of a main part of a bending tube.
Figure 11:
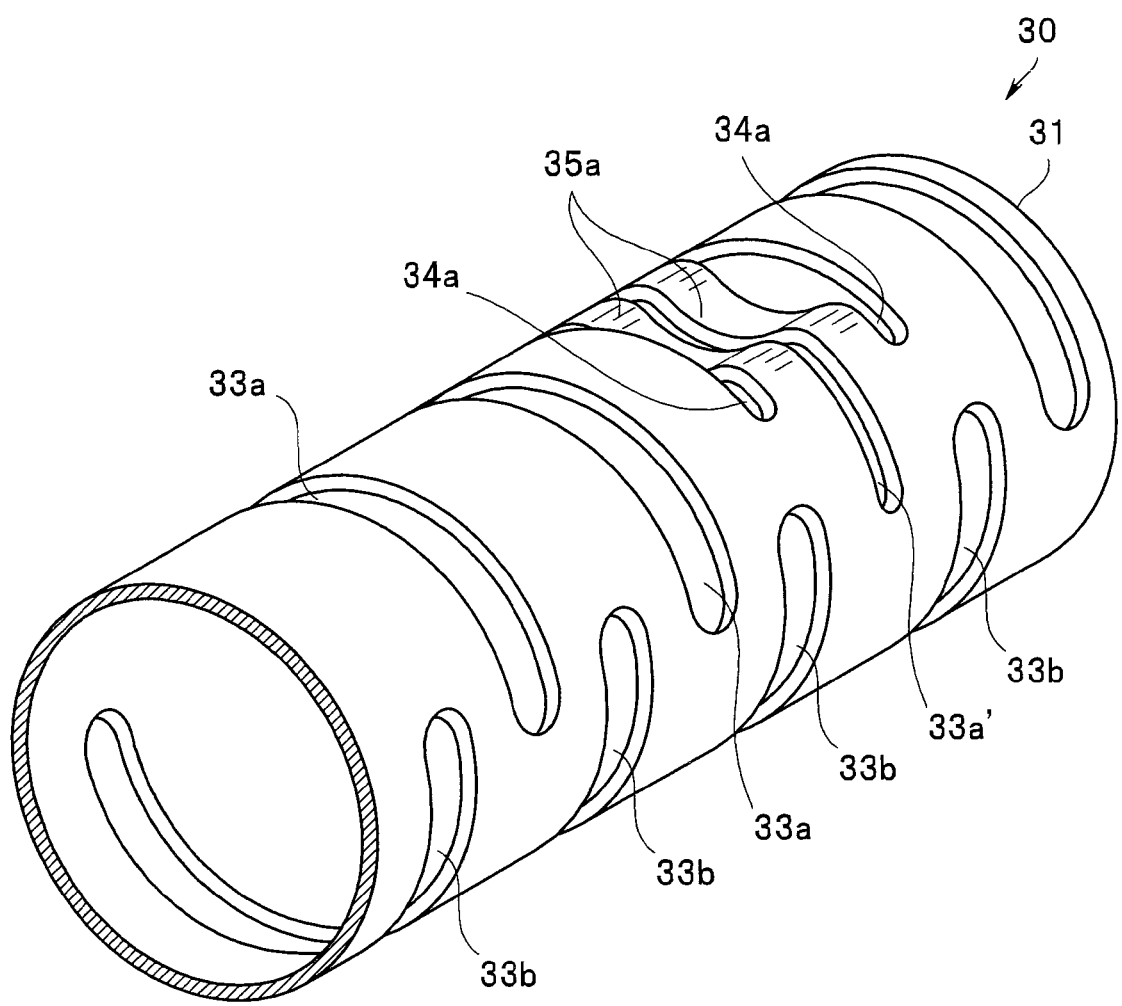
FIG. 11 relates to the third embodiment of the present invention and is a perspective view showing the main part of the bending tube.

Next, FIGS. 10 and 11 relate to a third embodiment of the present invention. FIG. 10 is a side view showing a cutaway of a portion of a main part of a bending tube, and FIG. 11 is a perspective view showing the main part of the bending tube. Note that the present embodiment is different from the first embodiment described above mainly in that slots for forming wire guide are provided separately from slots for bending 33a and 33b. As for other components similar to those of the first embodiment described above, the same reference numerals are given and description will be omitted. The configuration on the upside of a bending tube 30 and the configuration on the downside are almost similar. Therefore, in the present embodiment, mainly the configuration on the upside will be described, and description of the configuration on the downside will be appropriately omitted.

As shown in FIGS. 10 and 11, paired slots for forming wire guide 34a are provided at such positions that a particular slot for bending 33a', among the multiple slots for bending 33a, is located therebetween, on a bending tube body 31 of the present embodiment.

A part of the circumferential part of the bending tube body 31 is deformed in the inner diameter direction between the paired slots for forming wire guide 34a, and a wire guide 35a through which a middle part of an angle wire 19a is inserted is formed on the bending tube 30 by the deformation.

In the present embodiment in which the slots for forming wire guide 34a and 34b are provided separately as described above, the rigidity of the bending tube body 31 at a part where the slots for forming wire guide 34a and 34b are provided partially decreases because superelastic alloy material is used. Such partial decrease in the rigidity also affects the bending characteristic of the bending tube 30.

Due to formation of the wire guides 35a and 35b, a position of side walls before and after the particular slots for bending 33a' and 33b' coming into contact with each other is lower than a position of side walls before and after the other slots for bending 33a and 33b coming into contact with each other. Therefore, if a width H5 of the particular slots for bending 33a' and 33b' is set almost similar to a width H1 of the other slots for bending 33a and 33b, the timing of the front and back wall parts of the particular slots for bending 33a' and 33b' coming into contact with each other is later than the timing of the front and back wall parts of the other slots for bending 33a and 33b coming into contact with each other.

Therefore, in the present embodiment, the width H5 of the particular slots for bending 33a' and 33b' adjacent to the slots for forming wire guide 34a and 34b is set relatively narrower than the width H1 of the other slots for bending 33a and 33b, and the bending characteristic of the bending tube 30 is equalized by adjustment of the width H5.

According to such an embodiment, an effect is obtained that it is possible to decrease the number of the particular slots for bending 33a' and 33b' which require separate width adjustment, in addition to the effects obtained in the first embodiment described above.

Figure 12:
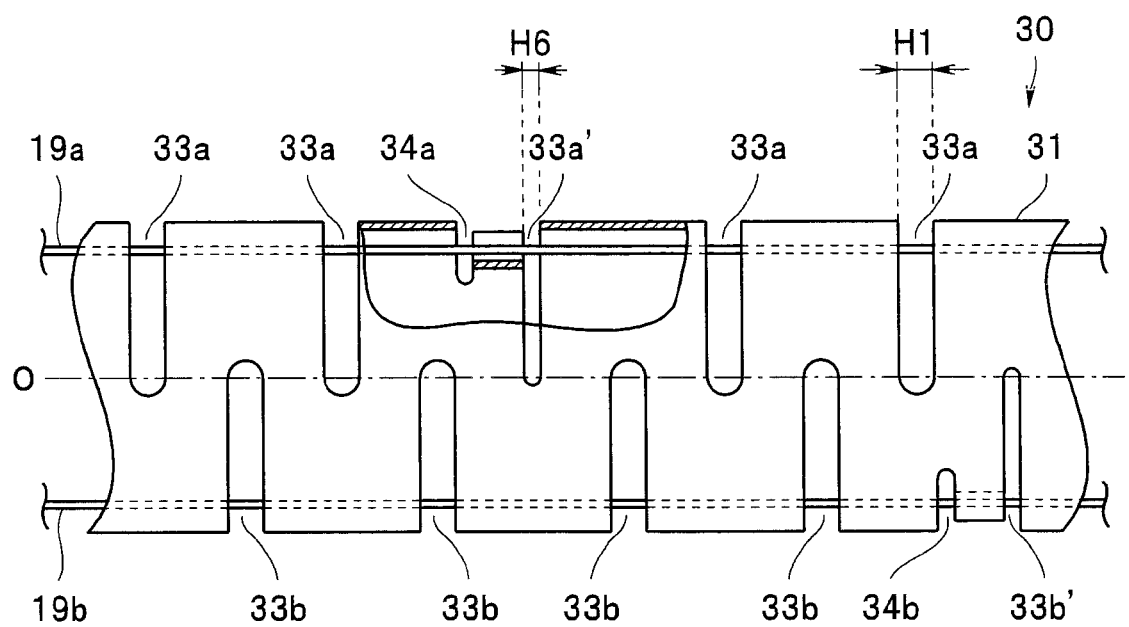
FIG. 12 relates to a fourth embodiment of the present invention and is a side view showing a main part of a bending tube, with a part thereof being cut off.
Figure 13:
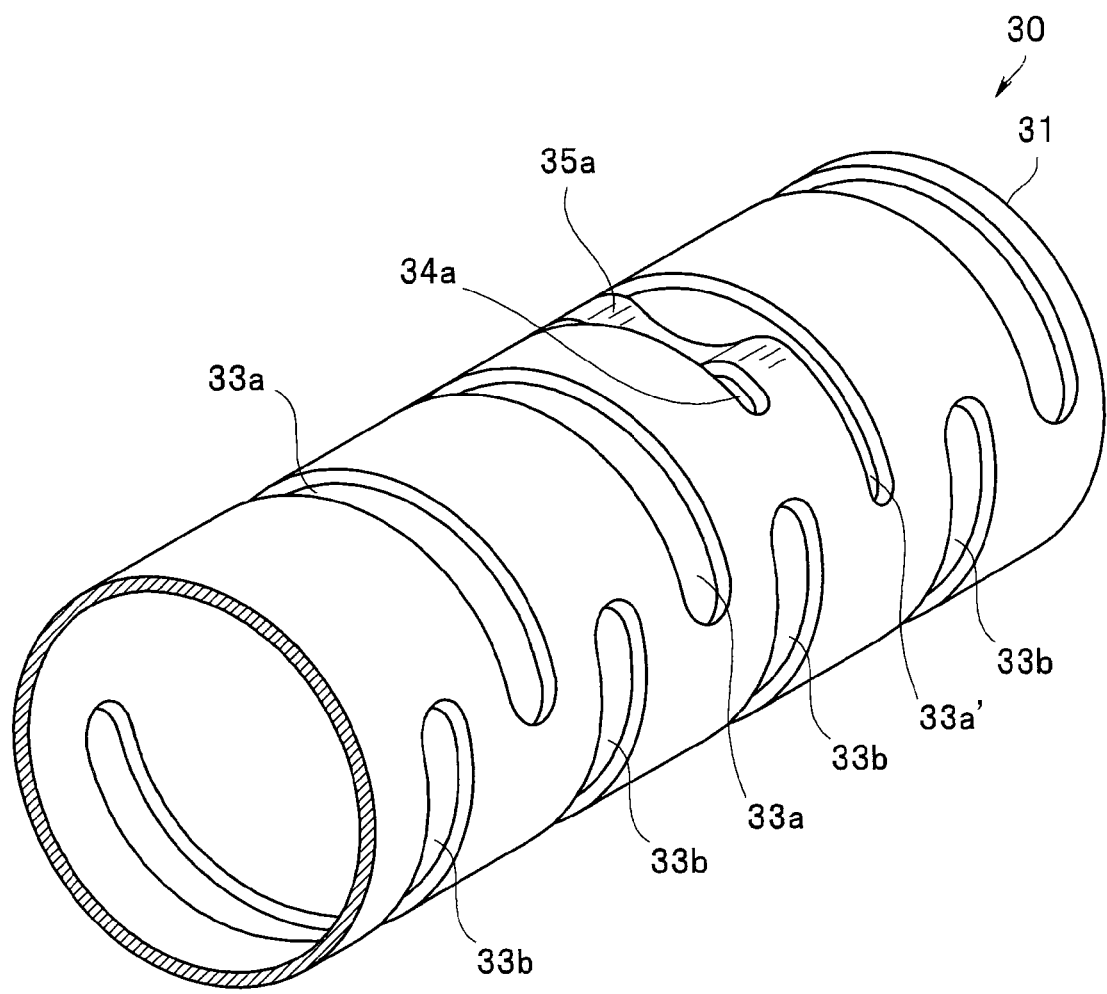
FIG. 13 relates to the fourth embodiment of the present invention and is a perspective view showing the main part of the bending tube.

Next, FIGS. 12 and 13 relate to a fourth embodiment of the present invention. FIG. 12 is a side view showing a main part of a bending tube, with a part thereof being cut off, and FIG. 13 is a perspective view showing the main part of the bending tube. Note that the present embodiment is different from the first embodiment described above mainly in that a slot for bending 33a or 33b is used as one of paired slots for forming wire guide, and the other is separately provided. As for other components similar to those of the first embodiment described above, the same reference numerals are given and description will be omitted. The configuration on the upside of a bending tube 30 and the configuration on the downside are almost similar. Therefore, in the present embodiment, mainly the configuration on the upside will be described, and description of the configuration on the downside will be appropriately omitted.

As shown in FIGS. 12 and 13, a particular slot for bending 33a', among multiple slots for bending 33a, is also used as one of paired slots for forming wire guide, on a bending tube body 31 of the present embodiment. On the bending tube body 31, the other slot for forming wire guide 34a (or slot for forming wire guide 34b) is provided at a position adjacent to the particular slots for bending 33a'.

A part of the circumferential part of the bending tube body 31 is deformed in the inner diameter direction between the particular slot for bending 33a' and the slot for forming wire guide 34a, and a wire guide 35a through which a middle part of an angle wire 19a is inserted is formed on the bending tube 30 by the deformation.

At the particular slots for bending 33a' and 33b', front and back wall parts are not level with each other. Therefore, if a width H6 of the particular slots for bending 33a' and 33b' is set almost similar to a width H1 of the other slots for bending 33a and 33b, the timing of the front and back wall parts of the particular slots for bending 33a' and 33b' coming into contact with each other is later than the timing of the front and back wall parts of the other slots for bending 33a and 33b coming into contact with each other.

In the present embodiment in which the slots for forming wire guide 34a and 34b are provided separately as described above, the rigidity of the bending tube body 31 at a part where the slots for forming wire guide 34a and 34b are provided partially decreases. Such partial decrease in the rigidity also affects the bending characteristic of the bending tube 30.

Therefore, in the present embodiment, the width H6 of the particular slots for bending 33a' and 33b' adjacent to the slots for forming wire guide 34a and 34b is set relatively narrower than the width H1 of the other slots for bending 33a and 33b, and the bending characteristic of the bending tube 30 is equalized by adjustment of the width H6.

According to such an embodiment, an effect is obtained that it is possible to decrease the number of the particular slots for bending 33a' and 33b' which require separate width adjustment, in addition to the effects obtained in the first embodiment described above.

Figure 14:
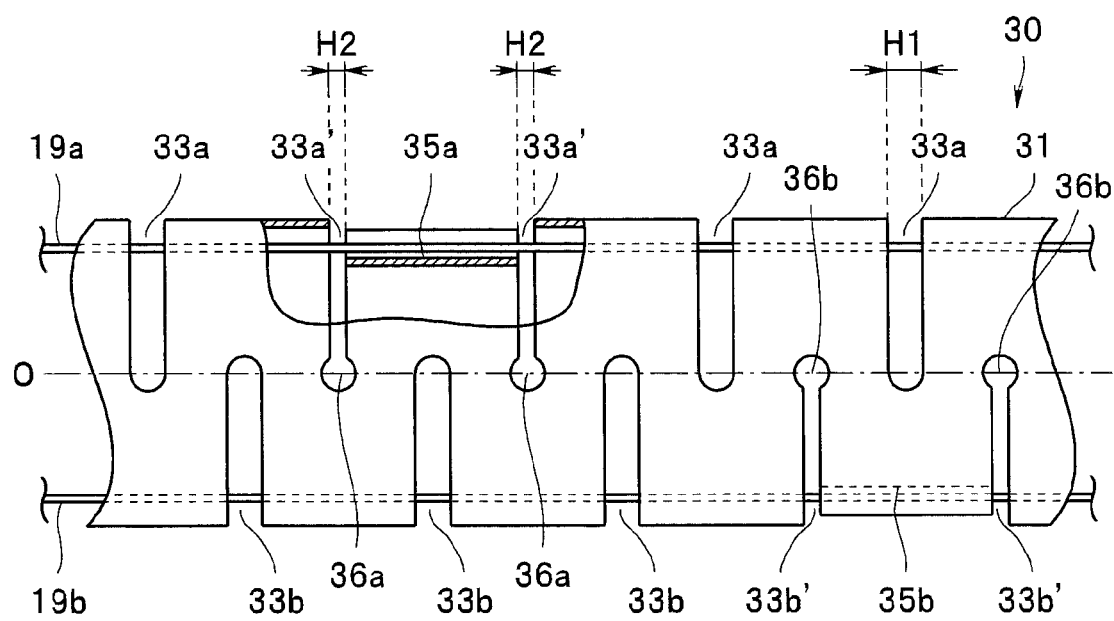
FIG. 14 relates to a fifth embodiment of the present invention and is a side view showing a cutaway of a portion of a main part of a bending tube.
Figure 15:
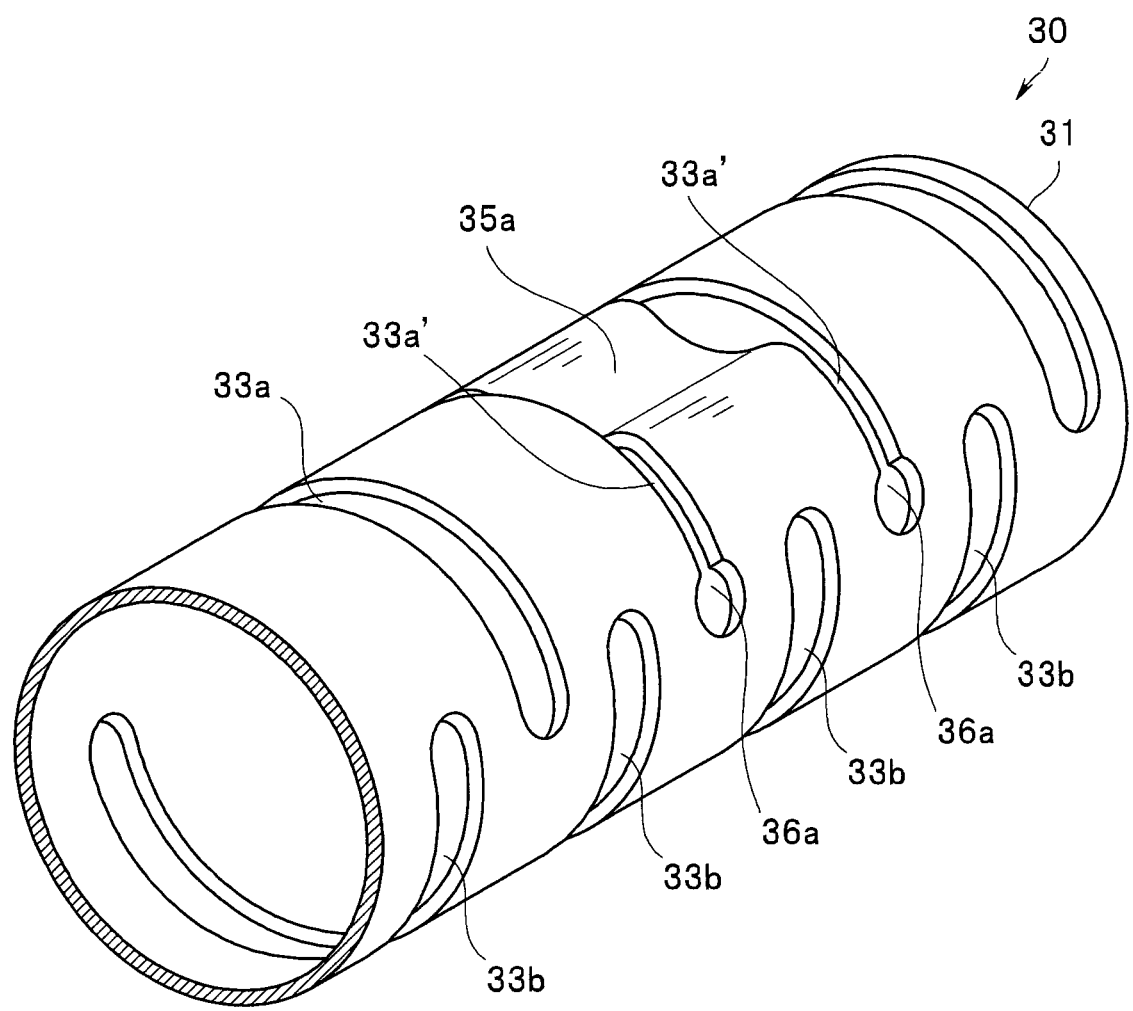
FIG. 15 relates to the fifth embodiment of the present invention and is a perspective view showing the main part of the bending tube.

Next, FIGS. 14 and 15 relate to a fifth embodiment of the present invention. FIG. 14 is a side view showing a cutaway of a portion of a main part of a bending tube, and FIG. 15 is a perspective view showing the main part of the bending tube. Note that the present embodiment is different from the first embodiment described above mainly in that through holes for strain relaxation 36a and 36b are provided at end parts of particular slots for bending 33a' and 33b'. As for other components similar to those of the first embodiment described above, the same reference numerals are given and description will be omitted. The configuration on the upside of a bending tube 30 and the configuration on the downside are almost similar. Therefore, in the present embodiment, mainly the configuration on the upside will be described, and description of the configuration on the downside will be appropriately omitted.

As shown in FIGS. 14 and 15, for example, the through holes for strain relaxation 36a and 36b formed in a circular hole are provided at end parts of the particular slots for bending 33a' and 33b' on a bending tube body 31 of the present embodiment. A diameter of the through holes for strain relaxation 36a and 36b is set relatively greater than a width H2 of the particular slots for bending 33a' and 33b'. More specifically, in the present embodiment, the diameter of the through holes for strain relaxation 36a and 36b is set equal to a width H1 of the other slots for bending 33a and 33b.

According to such an embodiment, it is possible to ensure, for the particular slots for bending 33a' and 33b' the width H2 of which is set relatively narrow, durability equal to that of the other slots for bending 33a and 33b by providing the through holes for strain relaxation 36a and 36b at the end parts of the particular slots for bending 33a' and 33b'. That is, though, as for the particular slots for bending 33a' and 33b' the width H2 of which is narrowed, stress due to strain at the time of bending is concentrated to the end parts of the slots in comparison with the other slots for bending 33a and 33b, it is possible to relax the concentration of stress by providing the through holes for strain relaxation 36a and 36b. Therefore, it is possible to, while ensuring a uniform bending characteristic, ensure durability to metal fatigue and the like similarly as the other slots for bending 33a and 33b even in the case of causing a bending movement and the like to be repeatedly performed.

Figure 16:
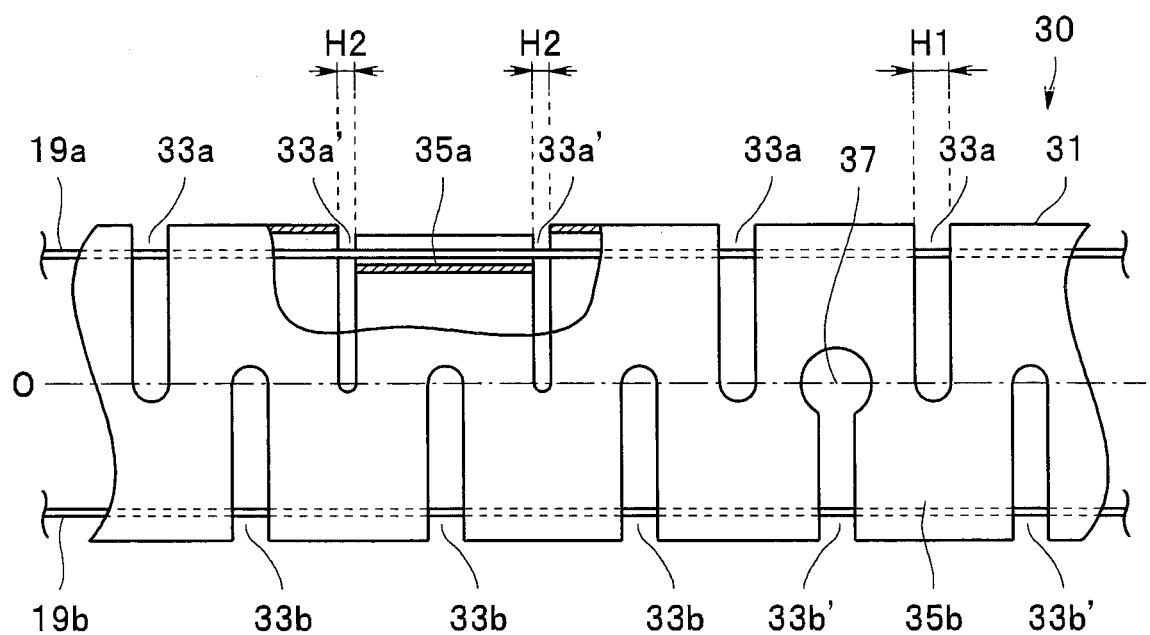
FIG. 16 relates to a sixth embodiment of the present invention and is a side view showing a cutaway of a portion of a main part of a bending tube.
Figure 17:
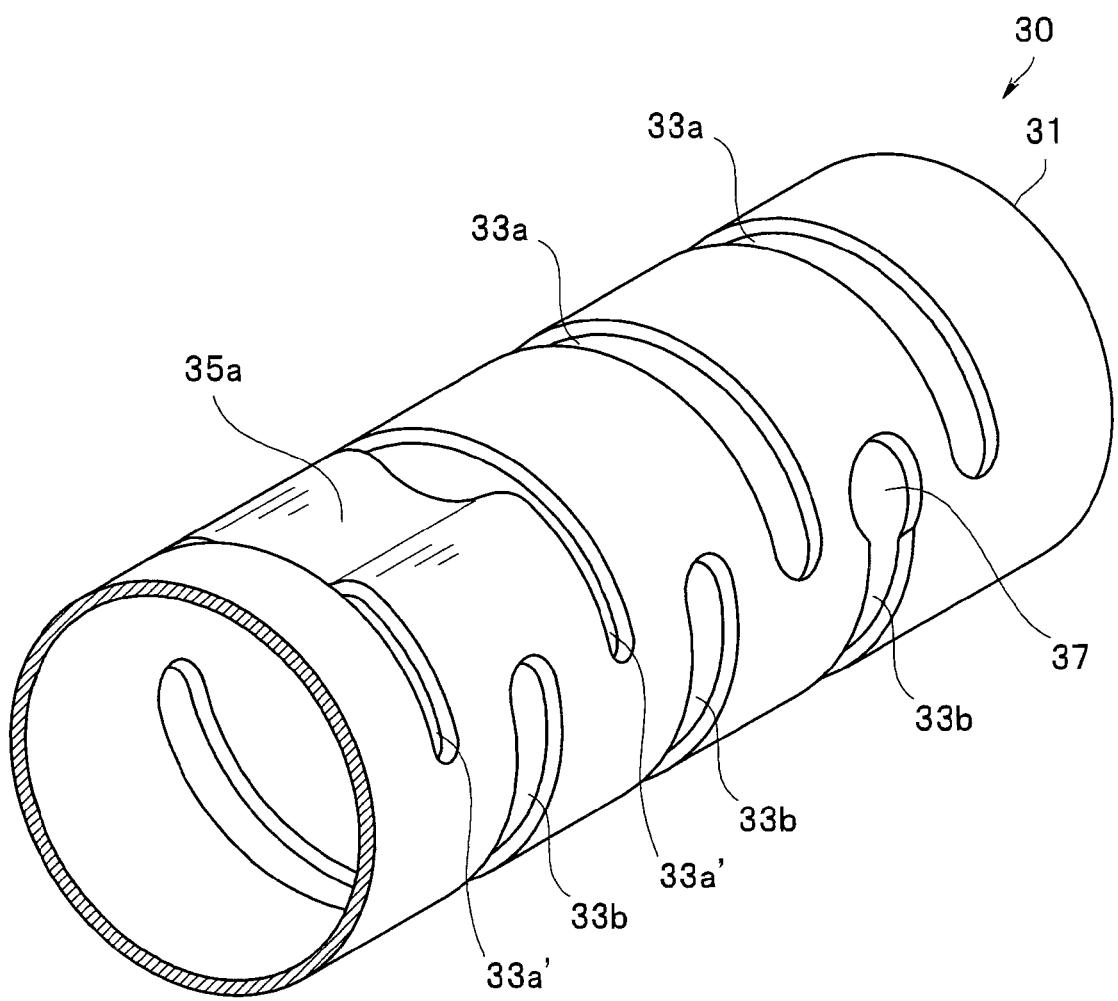
FIG. 17 relates to the sixth embodiment of the present invention and is a perspective view showing the main part of the bending tube.
Figure 18:
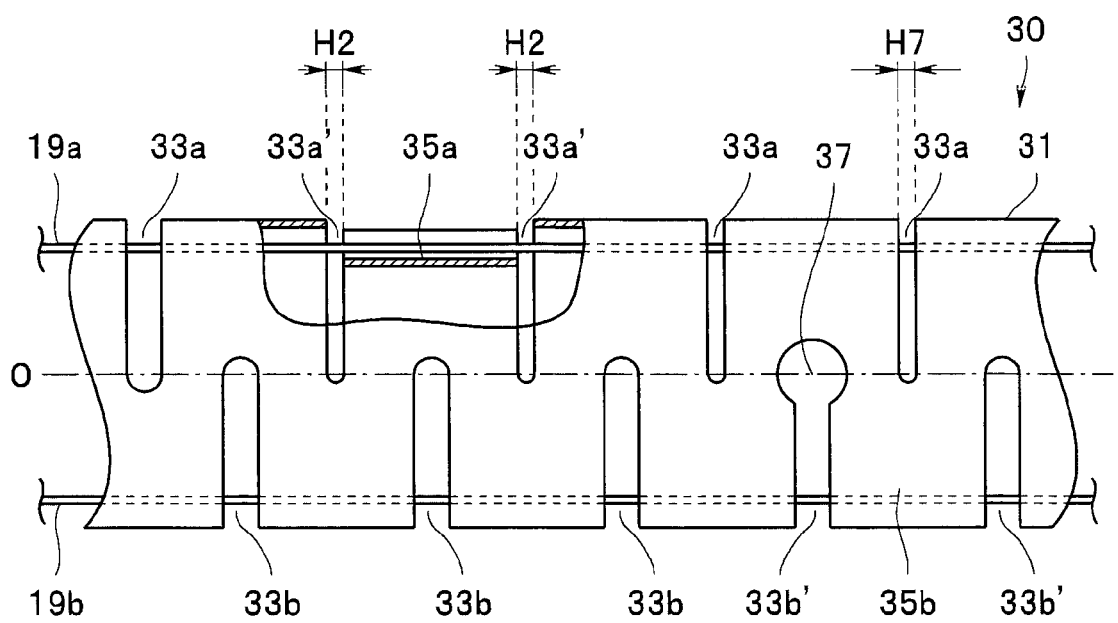
FIG. 18 relates to a first variation of the sixth embodiment of the present invention and is a side view showing a cutaway of a portion of a main part of a bending tube.
Figure 19:
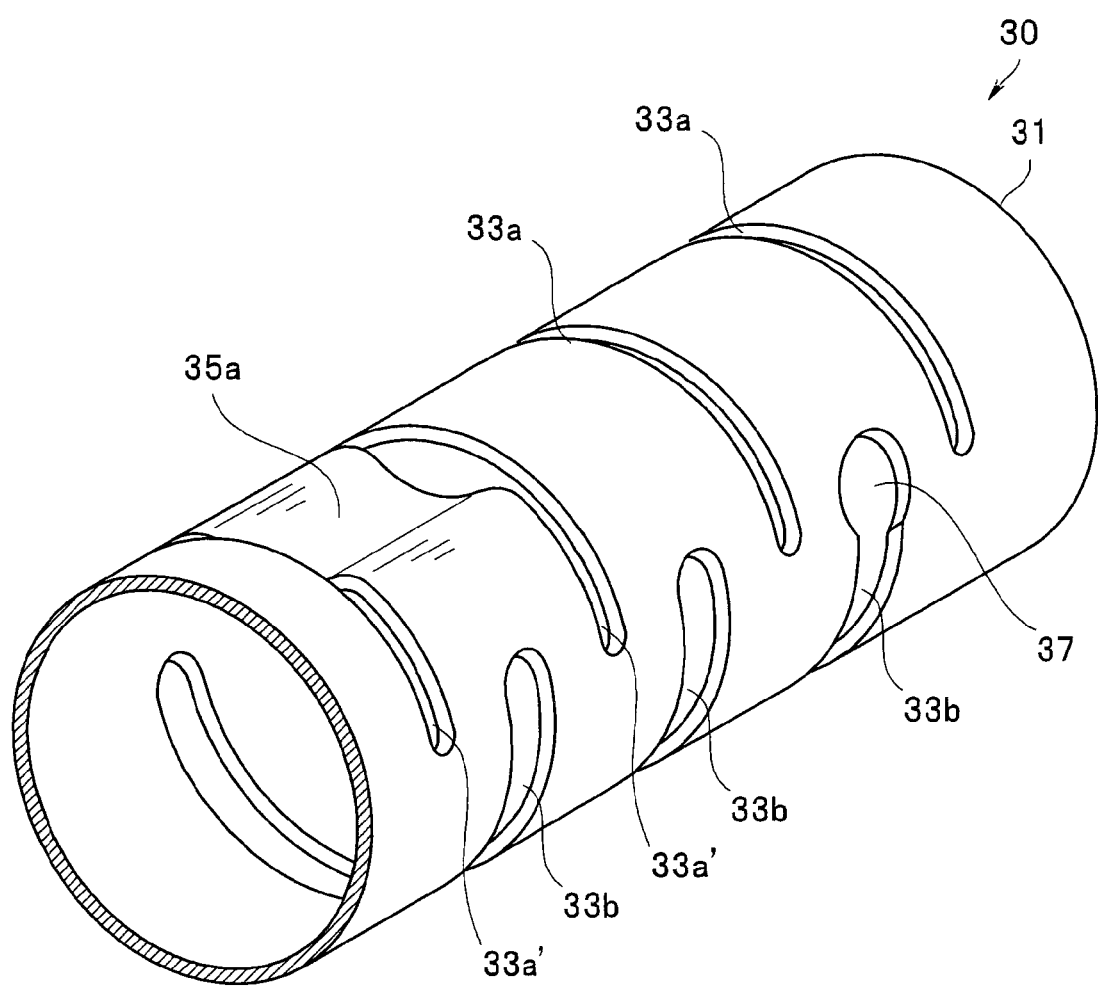
FIG. 19 relates to the first variation of the sixth embodiment of the present invention and is a perspective view showing the main part of the bending tube.
Figure 20:
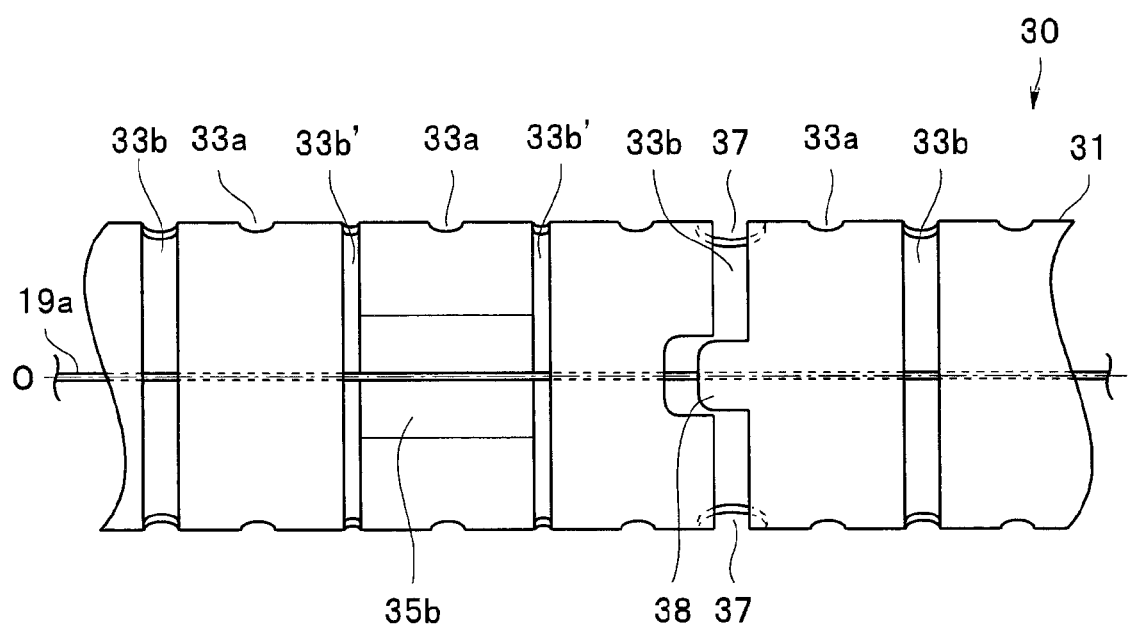
FIG. 20 relates to a second variation of the sixth embodiment of the present invention and is a bottom view showing a main part of a bending tube.
Figure 21:
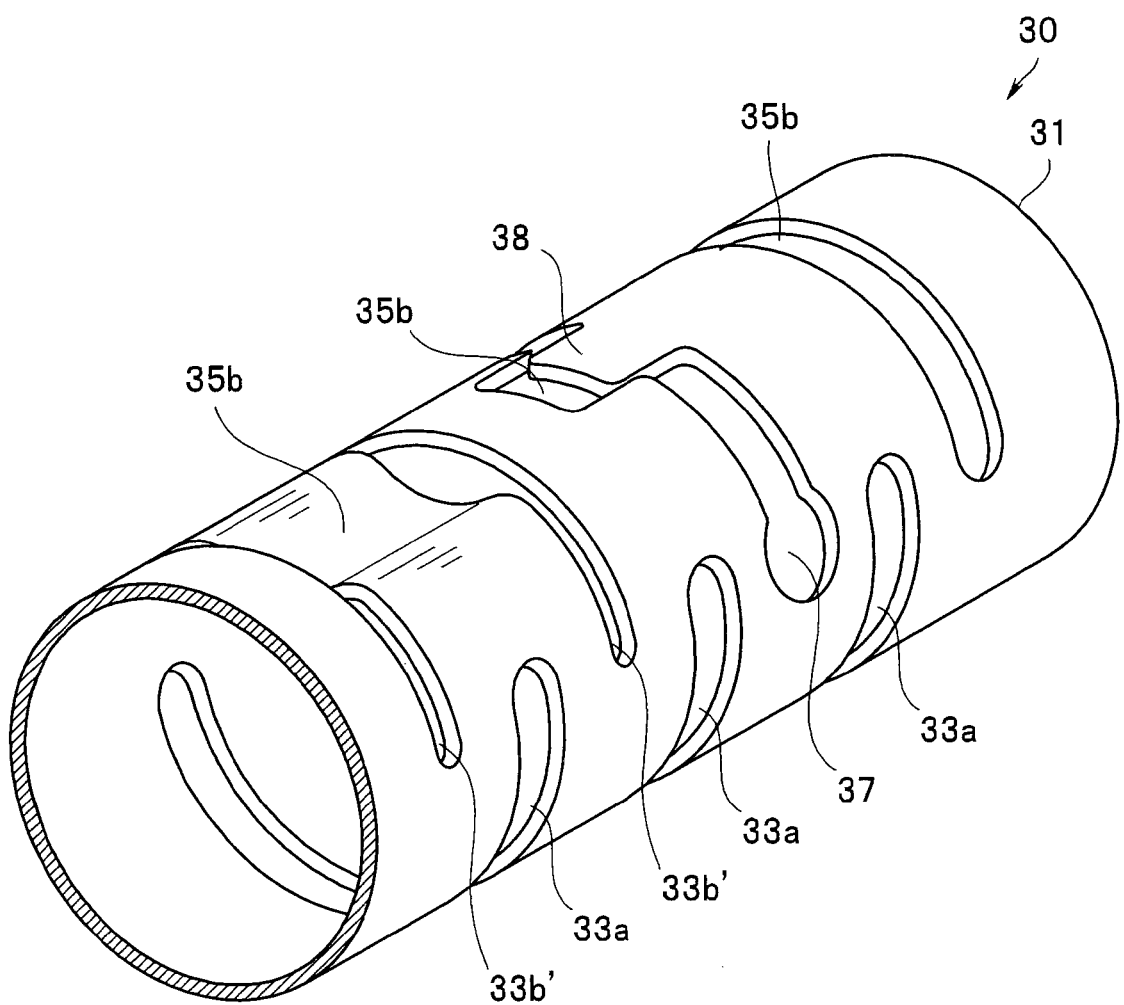
FIG. 21 relates to the second variation of the sixth embodiment of the present invention and is a perspective view showing the main part of the bending tube.

Next, FIGS. 16 to 22 relate to a sixth embodiment of the present invention. FIG. 16 is a side view showing a cutaway of a portion of a main part of a bending tube; FIG. 17 is a perspective view showing the main part of the bending tube; FIG. 18 relates to a first variation and is a side view showing a cutaway of a portion of a main part of a bending tube; FIG. 19 relates to the first variation and is a perspective view showing the main part of the bending tube; FIG. 20 relates to a second variation and is a top view showing a main part of a bending tube; FIG. 21 relates to the second variation and is a perspective view showing a main part of the bending tube; and FIG. 22 relates to a third variation and is a top view showing a main part of a bending tube. Note that the present embodiment mainly describes a configuration for improving workability at a time of forming wire guides 35a and 35b. As for other components similar to those of the first embodiment described above, the same reference numerals are given and description will be omitted.

As shown in FIGS. 16 and 17, a through hole for positioning 37 that passes through from one side to the other side is provided on a lateral part of a bending tube body 31 in the present embodiment. The through hole for positioning 37 is used for positioning of the bending tube body 31 against a processing jig not shown at the time of forming the wire guides 35a and 35b using the processing jig, for example.

In the present embodiment, the through hole for positioning 37 is provided, for example, at each of both end parts of the slots for bending 33b.

By providing such a through hole for positioning 37 at an appropriate position on the bending tube body 31, it becomes possible to perform positioning of the long bending tube body 31 against the processing jig accurately.

Since such a through hole for positioning 37 is configured by a hole part with a relatively long diameter, rigidity of a part where the through hole for positioning 37 is formed partially decreases on the bending tube body 31. When the rigidity partially decreases as described above, an elastic deformation amount partially increases, and a minimum radius of curvature of the part may be equal to or shorter than a bending radius determined by the width H1 of the slots for bending 33a.

Therefore, in the present embodiment, in order to correct such ununiformity of the bending characteristic, a width H7 of slots for bending 33a adjacent to the through holes for positioning 37 can be set relatively narrower than a width H1 of the other slots for bending 33a, for example, as shown in FIGS. 18 and 19.

When such a through hole for positioning 37 is provided, torsional rigidity around a longitudinal axis O of the bending tube body 31 also partially decreases.

Therefore, in the present embodiment, in order to compensate for such decrease in the torsional rigidity, a part of the slot for bending 33b having the through hole for positioning 37 can be formed in a crank shape to provide a torsion control tab 38.

Figure 22:
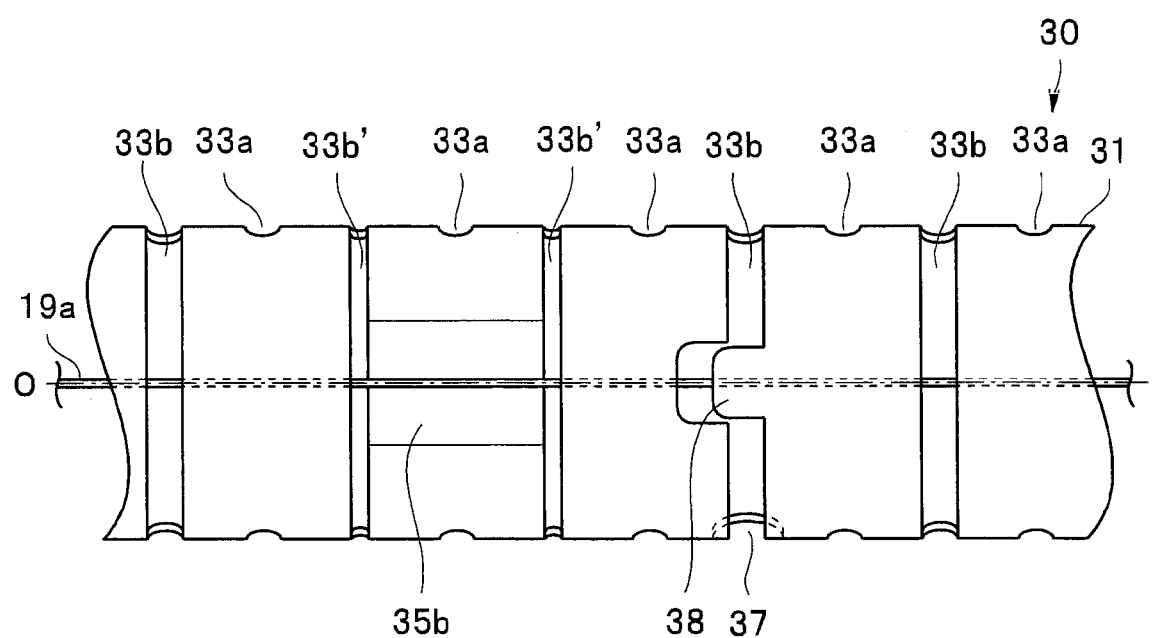
FIG. 22 relates to a third variation of the sixth embodiment of the present invention and is a bottom view showing a main part of a bending tube.

Though an example in which each through hole for positioning 37 is provided at both end parts of the slots for bending 33b has been described in the above description, it is also possible to provide the through hole for positioning 37 at one end part of the slots for bending 33b, for example, shown in FIG. 22, in order to prevent wrong assembly of the processing jig.

Note that, though an example in which the through hole for positioning 37 is provided at the end parts of the slots for bending 33b has been described in the present embodiment, it is, of course, possible to provide the through holes for positioning 37 at the end parts of the slots for bending 33a, on the contrary.

Figure 23:
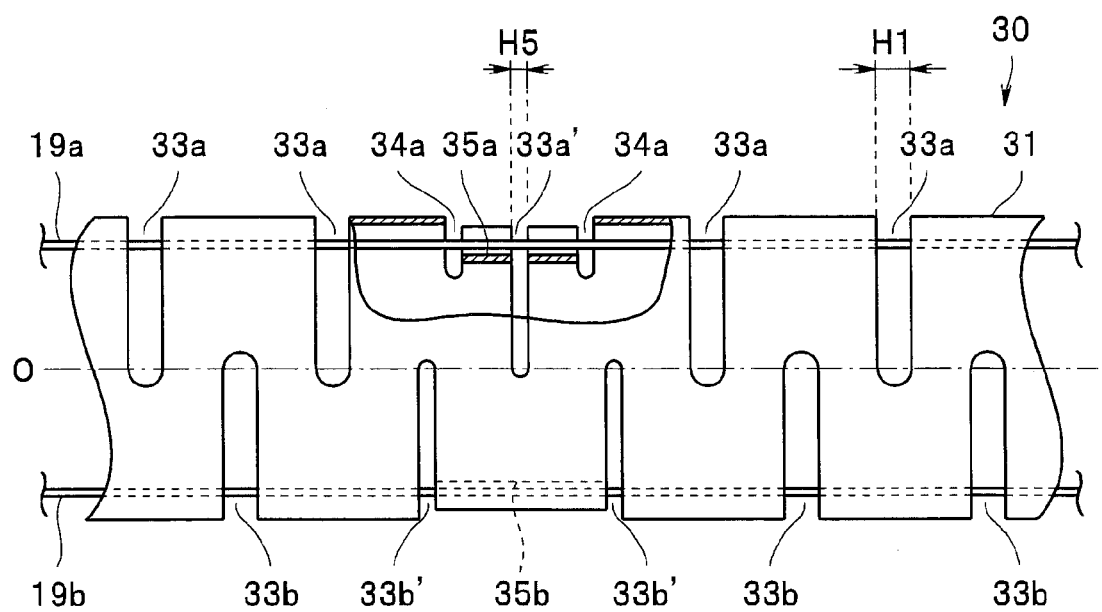
FIG. 23 is a side view showing a cutaway of a portion of a main part of a bending tube.
Figure 24:
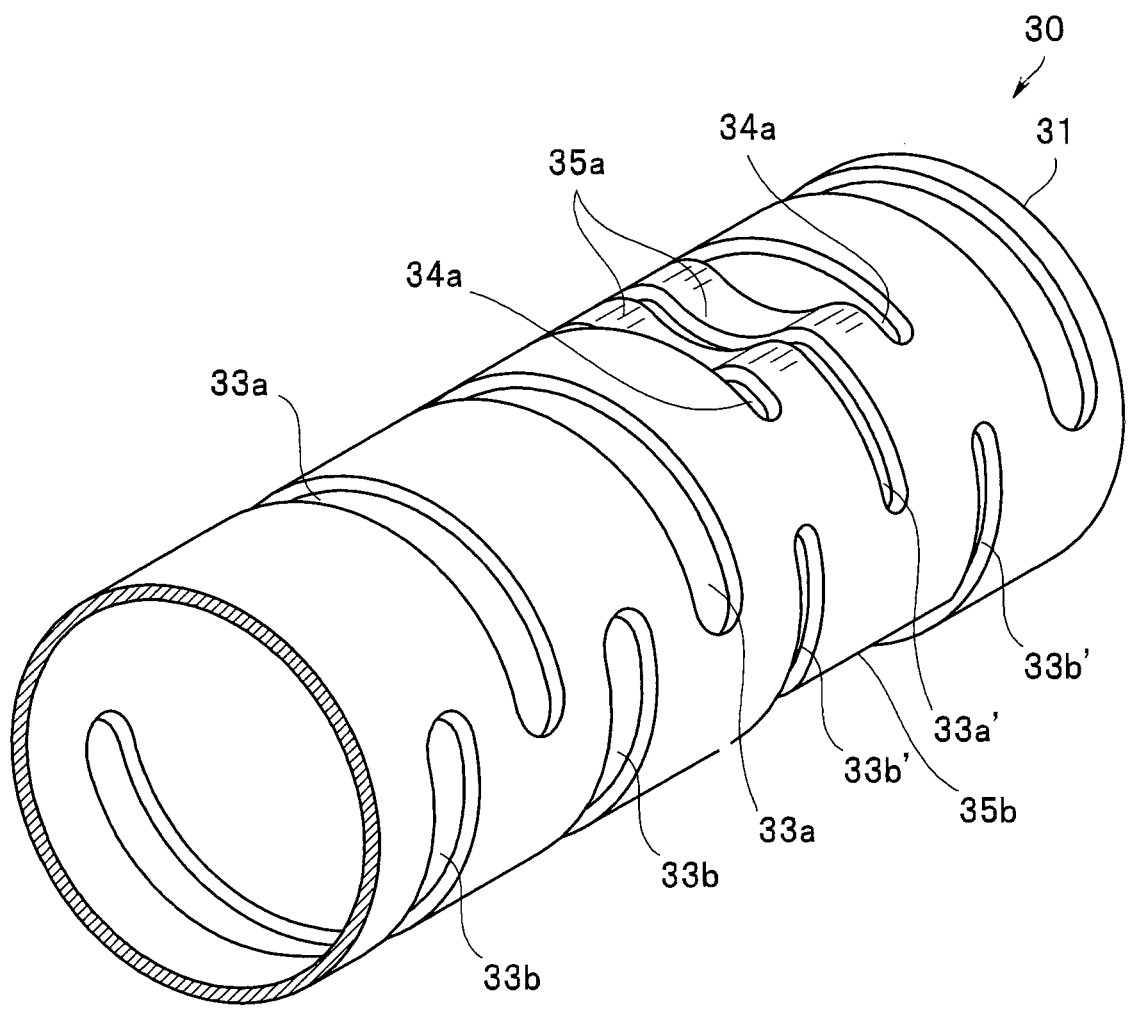
FIG. 24 is a perspective view showing a main part of the bending tube.

Note that the present invention is not limited to each embodiment described above, and various variations and modifications are possible. The various variations and modifications are also within the technical scope of the present invention. For example, the configuration shown in the first embodiment described above and the configuration shown in the third embodiment described above can be combined. That is, as shown in FIGS. 23 and 24, for example, it is also possible to form a wire guide 35a by providing paired slots for forming wire guide 34a at such a position that a particular slot for bending 33a', among multiple slots for bending 33a, is between the paired slots for forming wire guide 34a, on the upside of a bending tube body 31, and, on the other hand, form a wire guide 35b by using paired particular slots for bending 33b', among multiple slots for bending 33b, as slots for forming wire guide also, on the downside of the bending tube body 31. By making such a configuration, it is possible to press the wire guides 35a and 35b at the same position on the upside and the downside in a direction of a longitudinal axis O of the bending tube body 31, and, therefore, it is possible to make it difficult for a processing jig and the bending tube body 31 to incline at a time of pressing. For each embodiment described above, other various combinations and the like are, of course, possible though description thereof is omitted.

Figure 25:
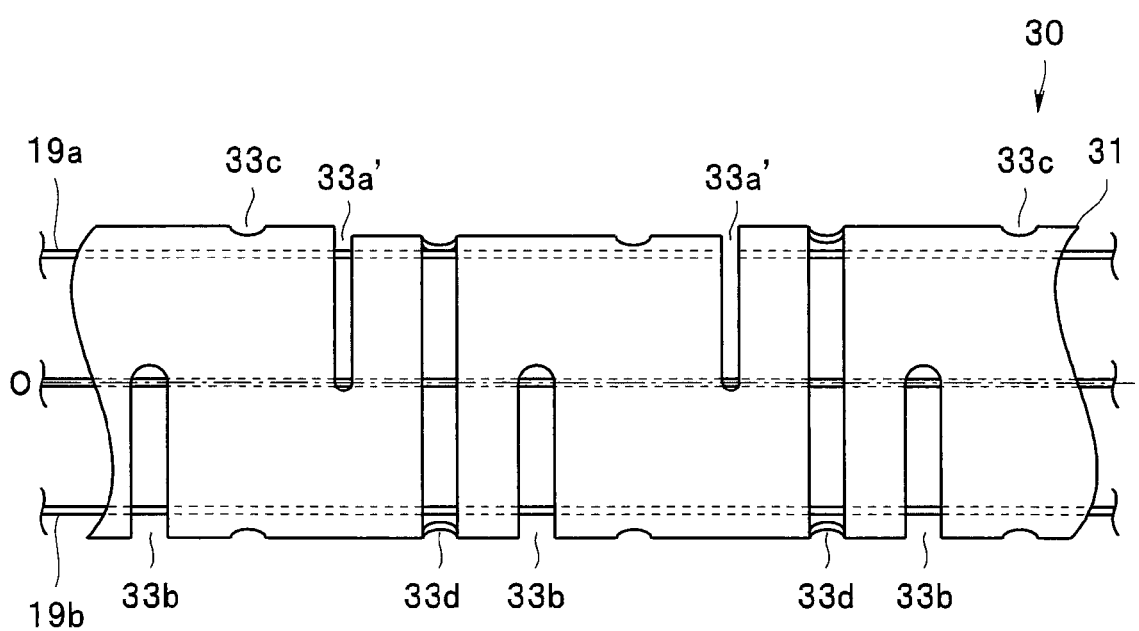
FIG. 25 is a side view showing a main part of a bending tube.

An example of a bending tube 30 bendable in two directions of up and down directions has been described in each embodiment described above. However, the present invention is not limited thereto. The present invention, of course, is also applicable to a bending tube 30 bendable in four directions of up, down, right and left directions, for example, as shown in FIG. 25. In this case, it is possible to adjust a width of a particular slot for bending or the like, among slots for bending 33c and 33d corresponding to bending in right and left directions, though it is not shown.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A bending tube for endoscope, the bending tube comprising:
 a cylindrical bending tube body made of superelastic alloy material;
 multiple slots for bending provided at set intervals, respectively, along a direction of a longitudinal axis of the bending tube body, the multiple slots for bending extending in a circumferential direction of the bending tube body; and
 a wire guide formed by deforming a circumferential part of the bending tube body between one or more pairs of adjacent slots for bending among the multiple slots for bending, in an inner diameter direction over an entire width between the one or more pairs of adjacent slots for bending; wherein
 a width of each of the one or more pairs of adjacent slots for bending is set narrower than a width of other of the multiple slots for bending.

2. The bending tube for endoscope according to claim 1, wherein a through hole for strain relaxation with a diameter greater than the width of the one or more pairs of adjacent slots for bending is provided at an end part of the one or more pairs of adjacent slots for bending.

3. The bending tube for endoscope according to claim 2, wherein the diameter of the through hole for strain relaxation corresponds to the width of the other of the multiple slots for bending.

4. The bending tube for endoscope according to claim 1, wherein the bending tube body is provided with a through hole for positioning at a time of forming the wire guide.

5. The bending tube for endoscope according to claim 4, wherein a width of a slot for bending, among the multiple slots for bending, adjacent to the through hole for positioning is set narrower than a width of the other of the multiple slots for bending.

6. The bending tube for endoscope according to claim 4, wherein a slot for bending, among the multiple slots for bending, having the through hole for positioning is provided with a tab for controlling torsion in a direction around the longitudinal axis of the bending tube body.

7. The bending tube for endoscope according to claim 2, wherein the through hole for strain relaxation is used as a through hole for positioning at a time of forming the wire guide in the bending tube body.

8. The bending tube for endoscope according to claim 4, wherein the through hole for positioning is a hole part having a diameter greater than the width of the one or more pairs of adjacent slots for bending, and is provided at an end part of the one or more pairs of adjacent slots for bending and thereby used as the through hole for strain relaxation.

9. The bending tube for endoscope according to claim 1, wherein the width of the one or more pairs of adjacent slots is set to a width such that a maximum folding angle of the bending tube body which the one or more pairs of adjacent slots for bending allows coincides with a maximum folding angle of the bending tube body which the other of the multiple slots for bending allow.

10. The bending tube for endoscope according to claim 1, wherein the width of the one or more pairs of adjacent slots is set to a width such that a maximum curvature of the bending tube body which the one or more pairs of adjacent slots for bending allows coincides with a maximum curvature of the bending tube body which the other of the multiple slots for bending allow.

* * * * *